(12) United States Patent
Okada et al.

(10) Patent No.: US 10,794,854 B2
(45) Date of Patent: Oct. 6, 2020

(54) MEASUREMENT DEVICE

(71) Applicant: LAPIS SEMICONDUCTOR CO., LTD., Kanagawa (JP)

(72) Inventors: Atsuhiko Okada, Kanagawa (JP); Kayoko Onitsuka, Kanagawa (JP)

(73) Assignee: LAPIS SEMICONDUCTOR CO., LTD., Yokohama (JP)

( * ) Notice: Subject to any disclaimer, the term of this patent is extended or adjusted under 35 U.S.C. 154(b) by 159 days.

(21) Appl. No.: 16/170,490

(22) Filed: Oct. 25, 2018

(65) Prior Publication Data

US 2019/0128839 A1 May 2, 2019

(30) Foreign Application Priority Data

Oct. 27, 2017 (JP) .................. 2017-208553

(51) Int. Cl.
*G01N 27/414* (2006.01)
*G01N 27/416* (2006.01)
*G01N 33/24* (2006.01)

(52) U.S. Cl.
CPC ....... *G01N 27/414* (2013.01); *G01N 27/4167* (2013.01); *G01N 33/24* (2013.01)

(58) Field of Classification Search
CPC .................. G01N 27/414; G01N 27/4167
See application file for complete search history.

(56) References Cited

U.S. PATENT DOCUMENTS

| 7,704,745 B2* | 4/2010 | Baudenbacher ... G01N 33/5005 422/82.01 |
| 8,197,650 B2* | 6/2012 | Kahn ................. A61B 5/14546 204/400 |
| 9,869,657 B2* | 1/2018 | King-Smith ....... G01N 27/4148 |

FOREIGN PATENT DOCUMENTS

| JP | 2009300272 A | 12/2009 |
| WO | 2011158812 A1 | 12/2011 |

* cited by examiner

*Primary Examiner* — Douglas M Menz
(74) *Attorney, Agent, or Firm* — Volentine, Whitt & Francos, PLLC

(57) ABSTRACT

There is provided a measurement device including: a first electrode and a second electrode that are configured to form an energization path via a measurement object at a front side and measure an electrical conductivity of the measurement object; and a reference electrode and an ISFET that are configured to measure a pH value of the measurement object, wherein a standard electrode of the reference electrode is disposed at a rear side of the first electrode and the second electrode.

7 Claims, 8 Drawing Sheets

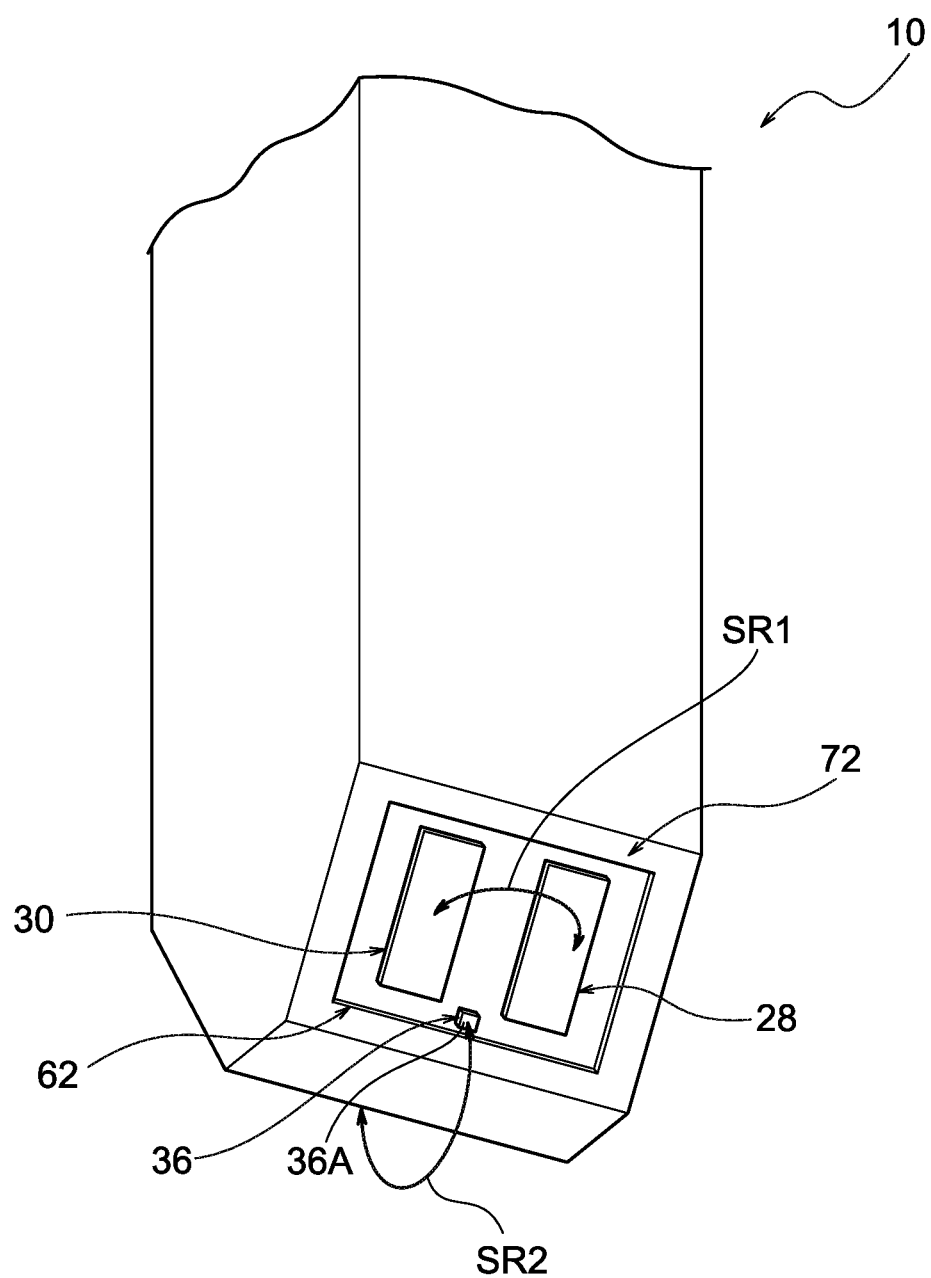

MEASUREMENT DEVICE

CROSS-REFERENCE TO RELATED APPLICATION

This application is based on and claims priority under 35 USC 119 from Japanese Patent Application No. 2017-208553 filed on Oct. 27, 2017, the disclosure of which is incorporated by reference herein.

BACKGROUND

Technical Field

The present disclosure relates to a measurement device that checks a state of a measurement object, such as soil.

Related Art

Management of soil is required to promote growth of a crop.

Examples of its management method include a method of managing so as to provide an environment in which a state of the soil is suitable for growing the crop, and measurements of a moisture content, an ionic concentration, and a pH value of the soil are required.

As a device for measuring a moisture content and an ionic concentration of soil, there is known a moisture state measurement device that measures an electrical conductivity of soil by paired electrodes (for example, refer to International Patent Application Laid-Open No. 2011/158812).

In addition, as a device that measures a pH value of soil, there is known a device that uses a reference electrode and an ISFET (for example, refer to Japanese Patent Application Laid-Open (JP-A) No. 2009-300272), but a measurement device that multilaterally measures a moisture content, an ionic concentration, and a pH value does not exist, and such a measurement device has been desired.

Hence, the present inventors have devised a measurement instrument including a pair of electrodes for measuring an electrical conductivity and a reference electrode and an ISFET for measuring a pH value.

However, with this measurement instrument, there occurs a problem that the reference electrode forming a standard electrode affects measurement of electrical conductivity by the pair of electrodes to reduce measurement accuracy.

SUMMARY

The invention has been made in view of such a problem and aims at providing a measurement device that can perform multilateral measurement while preventing the reference electrode from affecting the measurement.

The measurement device according to the disclosure includes a first electrode and a second electrode for forming an energization path via a measurement object at a front side and measuring an electrical conductivity of the measurement object, and a reference electrode and an ISFET for measuring a pH value of the measurement object, and a standard electrode of the reference electrode is disposed at a rear side of the first electrode and the second electrode.

According to the disclosure, it is possible to perform multilateral measurement while preventing the reference electrode from affecting the measurement.

BRIEF DESCRIPTION OF THE DRAWINGS

Exemplary embodiments of the present disclosure will be described in detail based on the following figures, wherein:

FIG. 8 is an explanatory diagram illustrating a use state of the measurement device according to one embodiment.

DETAILED DESCRIPTION

Figure 1:
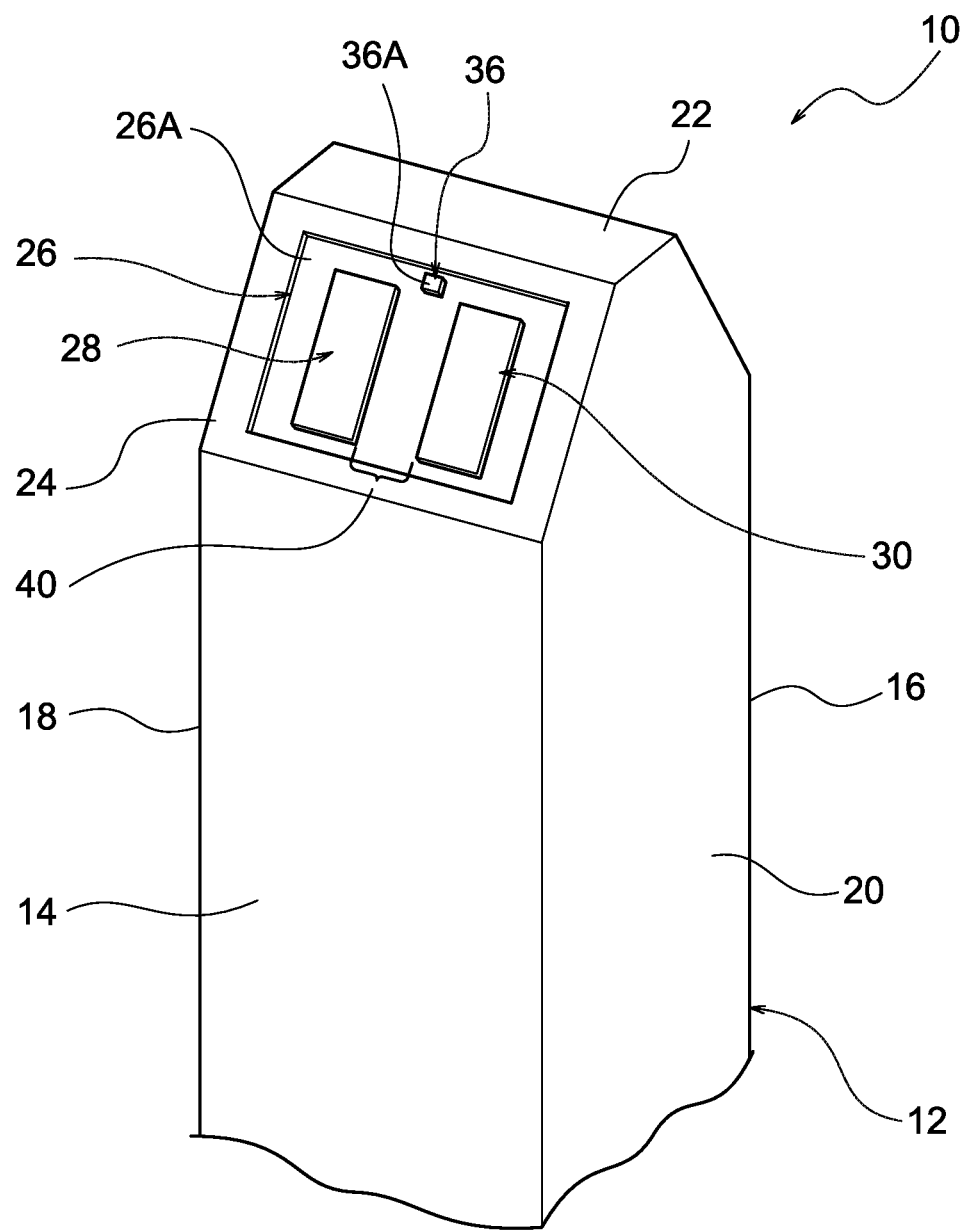
FIG. 1 is a perspective view illustrating a measurement device according to one embodiment.

One embodiment will be described below with reference to drawings. FIG. 1 is a view illustrating a measurement device 10 according to the present embodiment and the measurement device 10 is used for measuring a state of a measurement object ST (refer to FIG. 5 to FIG. 7), such as soil for growing a crop or nutritious liquid for hydroponic culture. In addition, the measurement device 10 includes two types of sensors and is configured to be capable of multi-laterally measuring a moisture content, an ionic concentration, a pH value, or the like of the measurement object ST.

Figure 2:
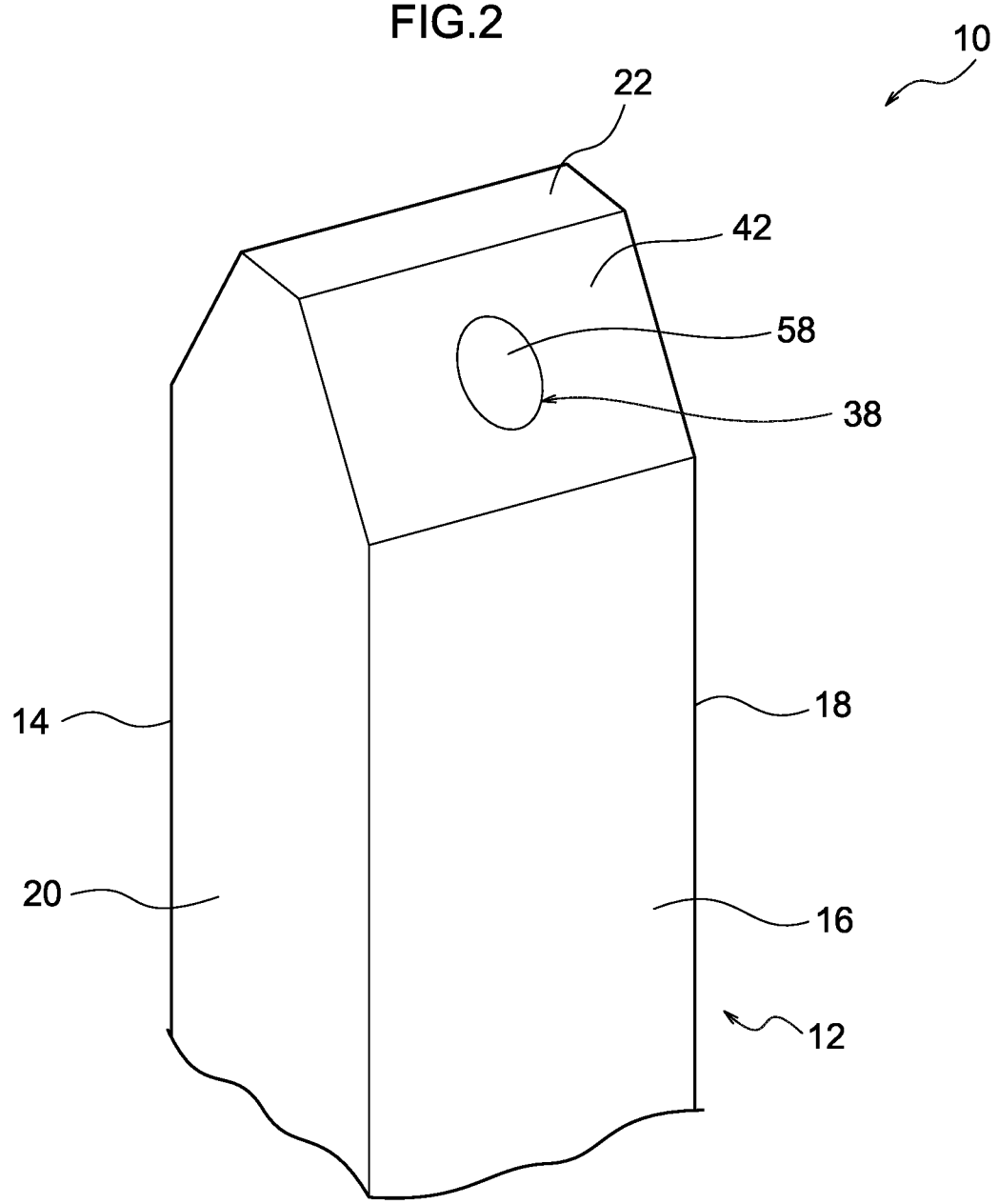
FIG. 2 is a perspective view illustrating the measurement device according to one embodiment when seen from a side opposite to that of FIG. 1.
Figure 3:
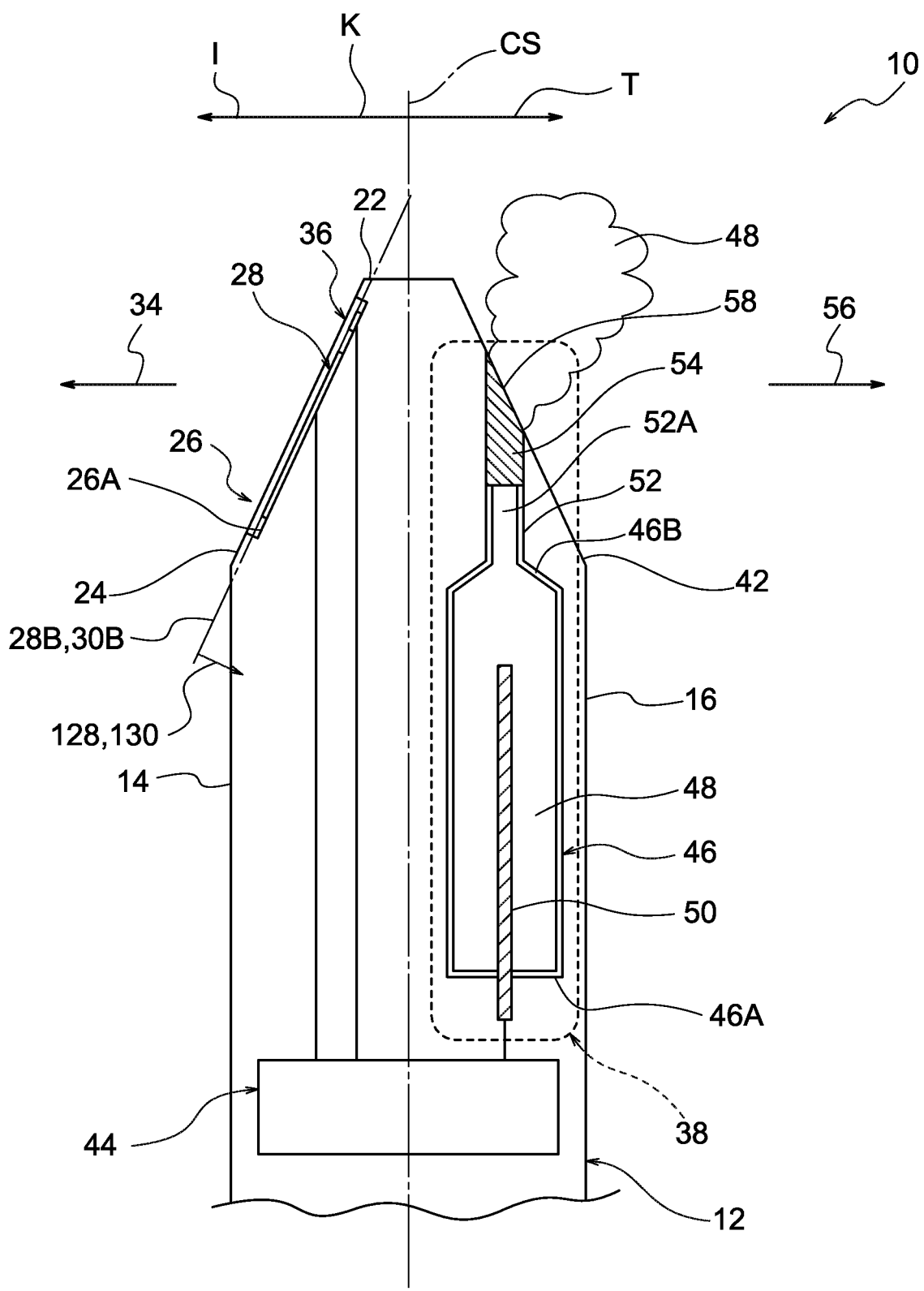
FIG. 3 is a sectional view illustrating the measurement device according to one embodiment.

A housing 12 of the measurement device 10 is formed of a synthetic resin that is an insulator, as one example. The housing 12 is, as shown in FIG. 1 to FIG. 3, for convenience sake, formed into a prismatic shape including a front surface 14 forming a front side, a rear surface 16 forming a rear side, a left surface 18 forming a left side, a right surface 20 forming a right side, and a tip surface 22 forming a tip side.

At a tip portion that is an upper side in FIG. 1 in the front surface 14 of the housing 12, as shown in FIG. 1, a front inclined surface 24 inclined to the rear surface 16 side toward the tip is formed. In the front inclined surface 24, a recessed portion 26 recessed in a rectangular shape is formed, and at the bottom of the recessed portion 26, a recessed-portion bottom surface 26A as one example of a flat surface is formed.

In the recessed-portion bottom surface 26A, a first electrode 28 and a second electrode 30 for measuring an electrical conductivity of the measurement object ST are arranged side by side apart from each other in right and left direction. Each electrode 28, 30 is formed into a rectangular plate shape and is fixed in a state in which a front surface faces the front side and a rear surface surface-contacts the recessed-portion bottom surface 26A.

The front surface of the first electrode 28 forms a plane contacting the measurement object ST and the first electrode 28 outputs an alternating-current signal. In addition, the front surface of the second electrode 30 has a plane contacting the measurement object ST and the second electrode 30 receives the alternating-current signal output from the first electrode 28 as an input signal.

Thus, each electrode 28, 30 is configured such that the front surface is made to be an energization surface, and at the time of measurement during which the measurement device 10 is inserted into the measurement object ST, an energization path 32 (refer to FIG. 7) via the measurement object ST is formed at a front side 34.

Figure 4:
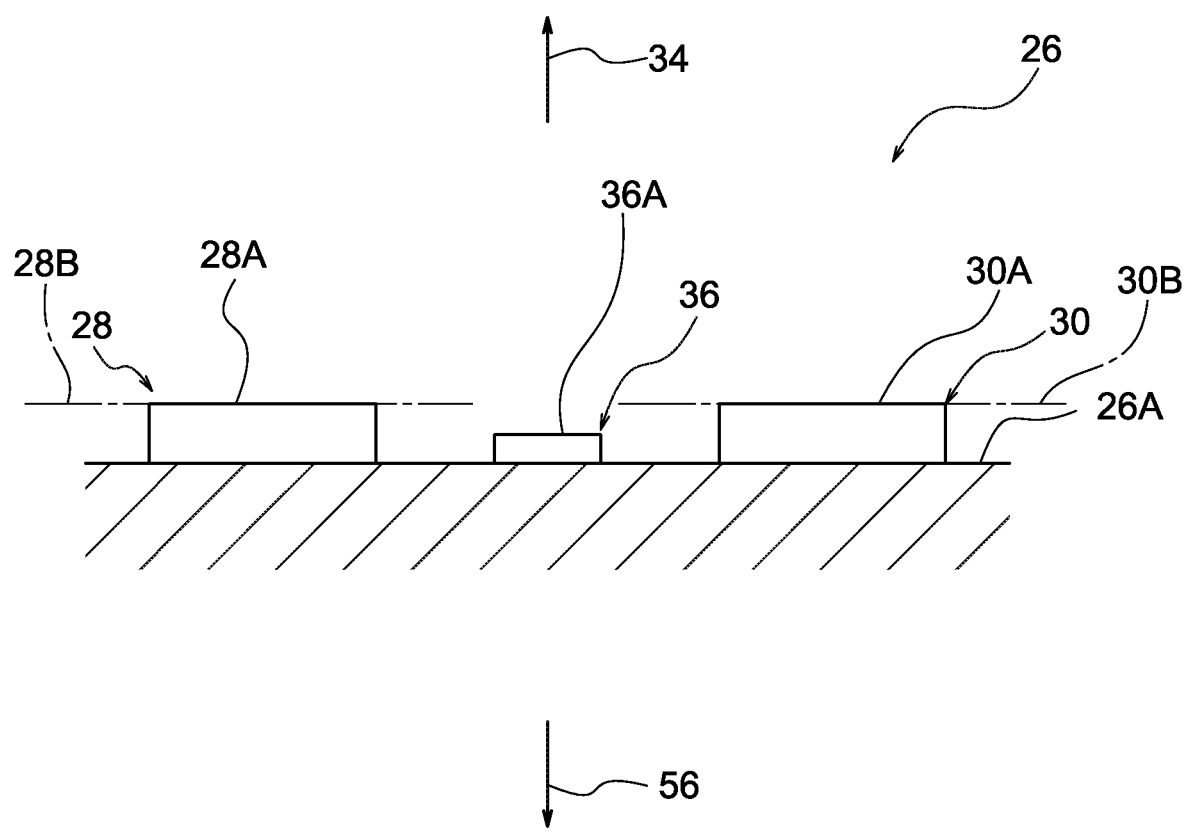
FIG. 4 is a sectional view of a main portion illustrating a recessed-portion bottom surface of the measurement device according to one embodiment.

At this time, as shown in FIG. 4, when a first virtual plane 28B that forms the same plane with the front surface of the first electrode 28 and a second virtual plane 30B that forms the same plane with the front surface of the second electrode 30 are assumed, each electrode 28, 30 is configured to be capable of measuring an electrical conductivity at a front side 34 of the both virtual planes 28B, 30B. Note that, in the present embodiment, as one example, the both virtual planes 28B, 30B form the same plane.

In addition, a rectangular ISFET (Ion Sensitive Field Effect Transistor) 36 is provided on the recessed-portion bottom surface 26A. The ISFET 36 is a chip used, together with a reference electrode 38 (refer to FIG. 3) to be described below, for measuring a pH value of the measurement object ST, and an external dimension of the ISFET 36 is smaller compared with the first electrode 28 and the second electrode 30.

The ISFET 36 is disposed closer to the tip than a separation region 40 between the first electrode 28 and the second electrode 30. As shown in FIG. 4, a sensitive surface 36A forming the front surface of the ISFET 36 is positioned closer to the recessed-portion bottom surface 26A than a first top surface 28A forming the front surface of the first electrode 28 and a second top surface 30A forming the front surface of the second electrode 30.

In the present embodiment, the ISFET 36 is made thinner than the first electrode 28 and the second electrode 30 and the sensitive surface 36A of the ISFET 36 is positioned closer to the recessed-portion bottom surface 26A than the first top surface 28A of the first electrode 28 and the second top surface 30A of the second electrode 30, but the present embodiment is not limited to this.

For example, by formation of a depression in the recessed-portion bottom surface 26A and by provision of the ISFET 36 in the depression, the sensitive surface 36A of the ISFET 36 may be positioned closer to the recessed-portion bottom surface 26A than the respective top surfaces 28A, 30A of the respective electrodes 28, 30.

As shown in FIG. 2, in the rear surface 16 of the housing 12, a rear inclined surface 42 inclined to the front surface 14 side toward the tip is formed at the tip portion on the upper side in FIG. 2, and the rear inclined surface 42 is formed flat.

The front inclined surface 24 described above is, as shown in FIG. 3, provided at one I side in an intersecting direction K intersecting with a virtual line CS, with respect to the virtual line CS that vertically cuts the housing 12 passing through the tip surface 22, which is one example of a vertex or a top surface positioned at the most tip side of the housing 12. Thereby, the recessed-portion bottom surface 26A formed in the front inclined surface 24 forms a first surface provided at the one I side with the virtual line CS as a boundary. In addition, the rear inclined surface 42 is provided at another T side in the intersecting direction K intersecting with the virtual line CS, and the rear inclined surface 42 forms a second surface at the another T side in the intersecting direction K.

Note that, the present embodiment shows, as an example, a case in which the virtual line CS is formed with a center line that vertically cuts the housing 12. In addition, for example, in a case in which a top portion of the housing 12 is formed with a spherical surface, the virtual line CS may be a straight line that passes through a vertex positioned at the most tip side in the housing 12.

Inside the housing 12, the reference electrode 38 and a control unit 44 are provided.

The reference electrode 38 includes a container-shaped tank 46, and an internal liquid 48 is filled inside the tank 46. An internal electrode 50 is disposed in the internal liquid 48, and a base end portion of the internal electrode 50 extends from a tank bottom surface 46A. Examples of the internal liquid 48 include potassium chloride (KCl) solution, and examples of a material of the internal electrode 50 include silver/silver chloride (Ag/AgCl).

A ceiling face 46B of the tank 46 is inclined to the tip side toward the central portion and a cylindrical tube portion 52 extends from its top portion. A communicating hole 52A in the tube portion 52 communicates with the inside of the tank 46 and is configured to be capable of supplying the internal liquid 48 inside the tank 46 from the tip of the tube portion 52 to a liquid communication portion 54.

At the tip of the tube portion 52, the columnar liquid communication portion 54 is provided, and the liquid communication portion 54 is formed of porous material. The tip portion of the liquid communication portion 54 is formed into a tapered shape which is cut obliquely, and its end face is exposed to the rear inclined surface 42. The reference electrode 38 is disposed such that the end face becomes flush with the rear inclined surface 42.

Thus, the reference electrode 38 is provided on the rear inclined surface 42 at the another T side in the intersecting direction K intersecting with the virtual line CS that vertically cuts the housing 12. Further, on the recessed-portion bottom surface 26A at the one I side in the intersecting direction K, the first electrode 28 and the second electrode 30 are provided, and the reference electrode 38 is disposed at a rear side 56 of the first electrode 28 and the second electrode 30.

In other words, the reference electrode 38 is disposed closer to a rear surface 128 of the first electrode 28 than the first virtual plane 28B that forms the same plane as the front surface of the first electrode 28 and closer to a rear surface 130 of the second electrode 30 than the second virtual plane 30B that forms the same plane as the front surface of the second electrode 30.

In addition, the reference electrode 38 supplies the internal liquid 48 inside the tank 46 from the tube portion 52 to the liquid communication portion 54, and the liquid communication portion 54 exudes the internal liquid 48 from the end face to the outside of the housing 12. The end face of the liquid communication portion 54 exposed to the rear inclined surface 42 forms a standard electrode 58 that imparts a standard potential to the measurement object ST.

The internal electrode 50 extended from the tank 46 of the reference electrode 38 is connected to the control unit 44.

Figure 5:
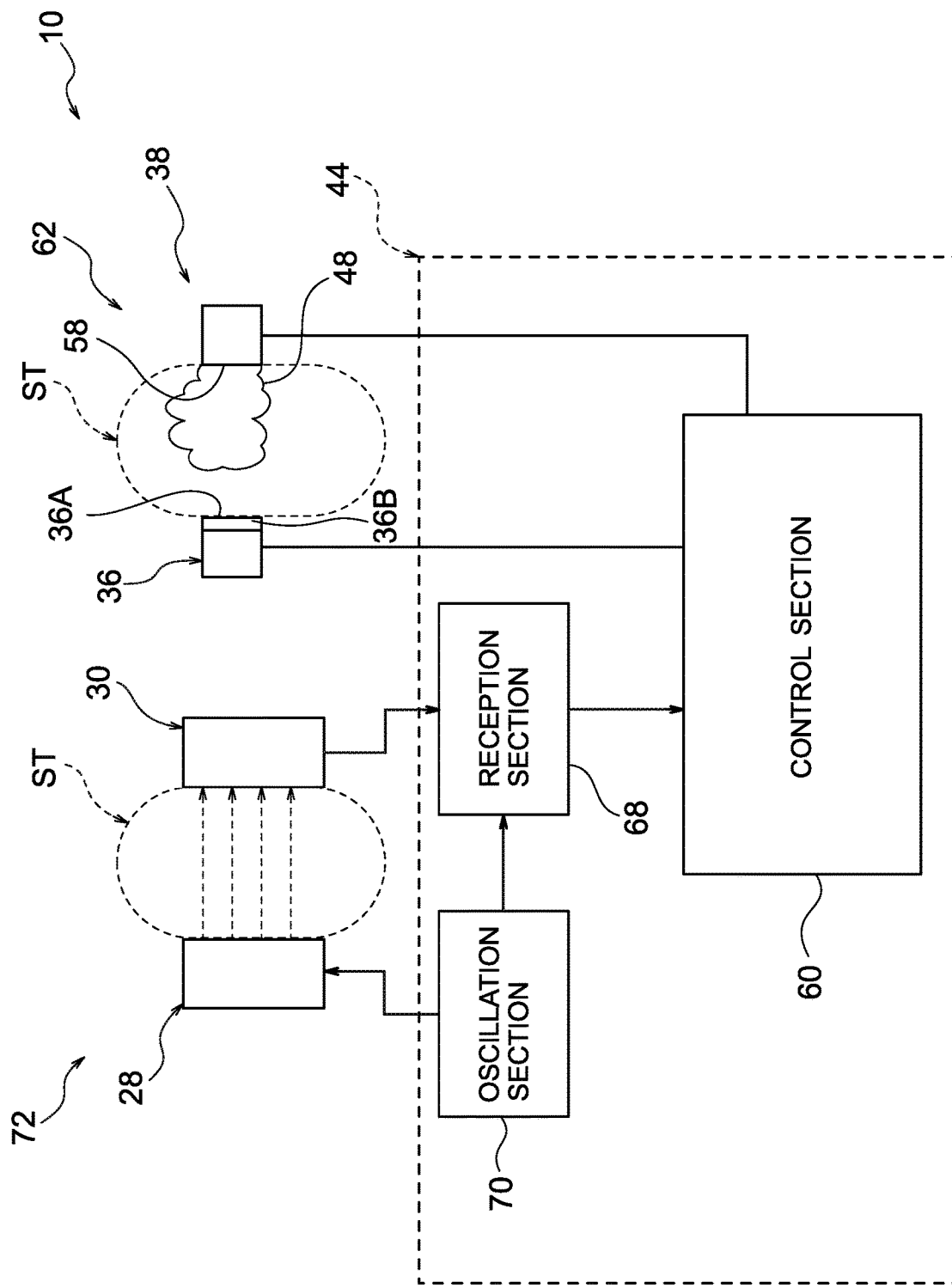
FIG. 5 is a block diagram illustrating the measurement device according to one embodiment.

The control unit 44, as shown in FIG. 5, includes a control section 60, the control section 60 is, for example, composed mainly of a microcomputer incorporating a ROM and a RAM. The control section 60 is connected with the internal electrode 50 of the reference electrode 38 (refer to FIG. 3) and the ISFET 36 forming a pair with the reference electrode 38, and a pH sensor 62 is composed of the reference electrode 38, the ISFET 36, and the control section 60.

Figure 6:
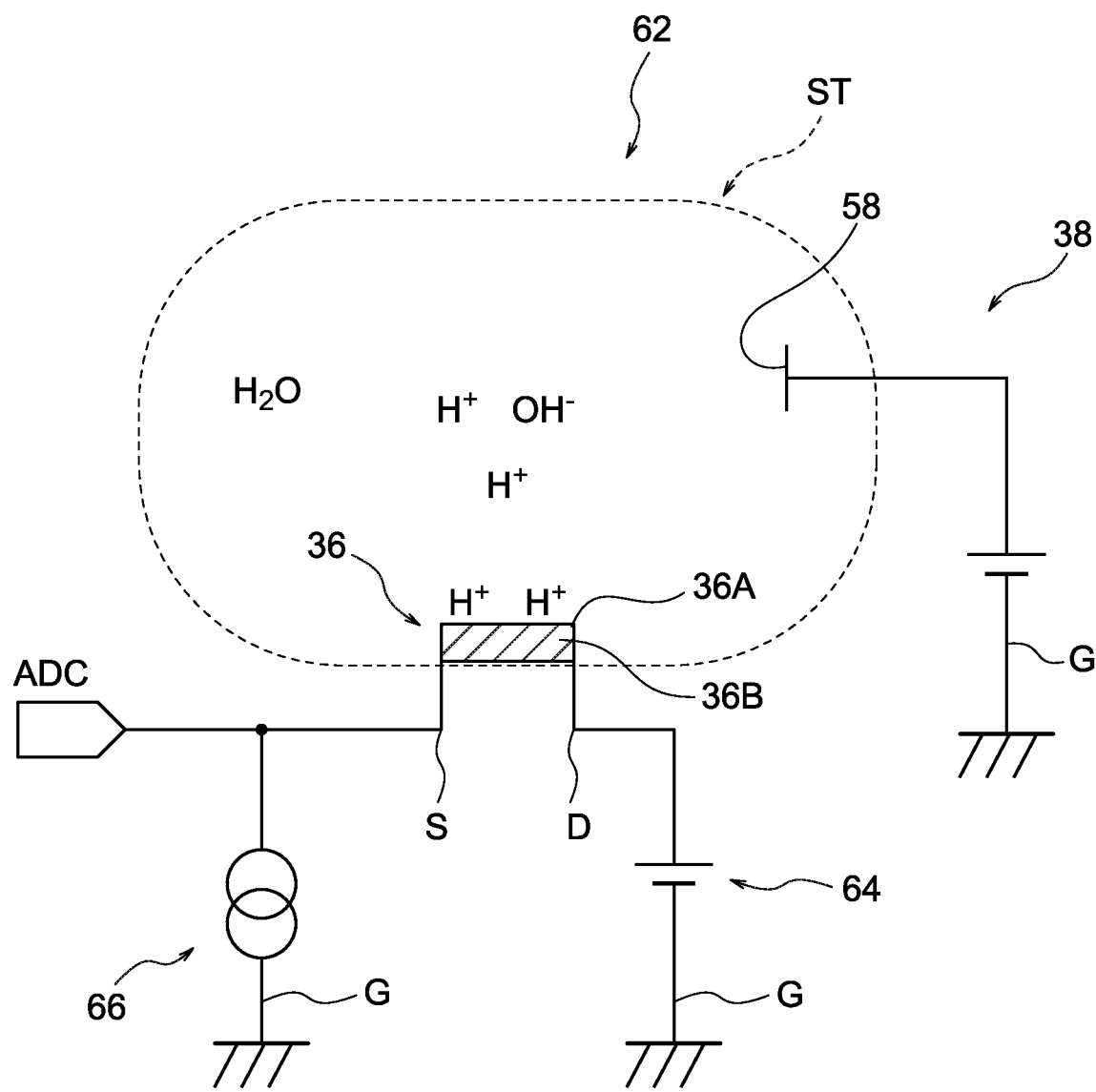
FIG. 6 is an explanatory diagram illustrating a pH sensor of the measurement device according to one embodiment.

The ISFET 36, as shown in FIG. 6, has a drain D connected with a positive electrode of a DC power source 64 and a source S grounded to a ground line G via a constant current circuit 66 and connected to an AD conversion port of, for example, a microcomputer forming the control section 60 (refer to FIG. 5). A gate portion between the drain D and source S of the ISFET 36 includes an ion-sensitive membrane 36B, and the ion-sensitive membrane 36B is configured such that its sensitive surface 36A contacts the measurement object ST.

When a standard potential of the reference electrode 38 is applied from the standard electrode 58 to the measurement object ST, hydrogen ions ($H^+$) in the measurement object ST gather on the sensitive surface 36A of the ISFET 36. Then, the ISFET 36 detects an interface potential between the measurement object ST and the ion-sensitive membrane 36B and flows a current. The control section 60 measures a pH value indicating a hydrogen ion exponent of the measurement object ST by measuring a potential difference between the interface potential detected by the ISFET 36 and the reference electrode 38.

In addition, as shown in FIG. 5, a reception section 68 is connected to the control section 60, and an alternating-current signal from an oscillation section 70 is supplied to the reception section 68. The first electrode 28 is connected to the oscillation section 70, and the first electrode 28, the front surface of which contacts the measurement object ST, outputs an alternating-current signal to the measurement object ST.

The second electrode 30 forming a pair with the first electrode 28 is also configured such that the front surface of the second electrode 30 contacts the measurement object ST, and the second electrode 30 is connected to the reception section 68. Thereby, the second electrode 30 receives the alternating-current signal output from the first electrode 28 to the measurement object ST as an input signal.

An electrical conductivity measurement sensor 72 includes the first electrode 28, the second electrode 30, the oscillation section 70, and the reception section 68, and a signal from the electrical conductivity measurement sensor 72 is sent to the control section 60.

Figure 7:
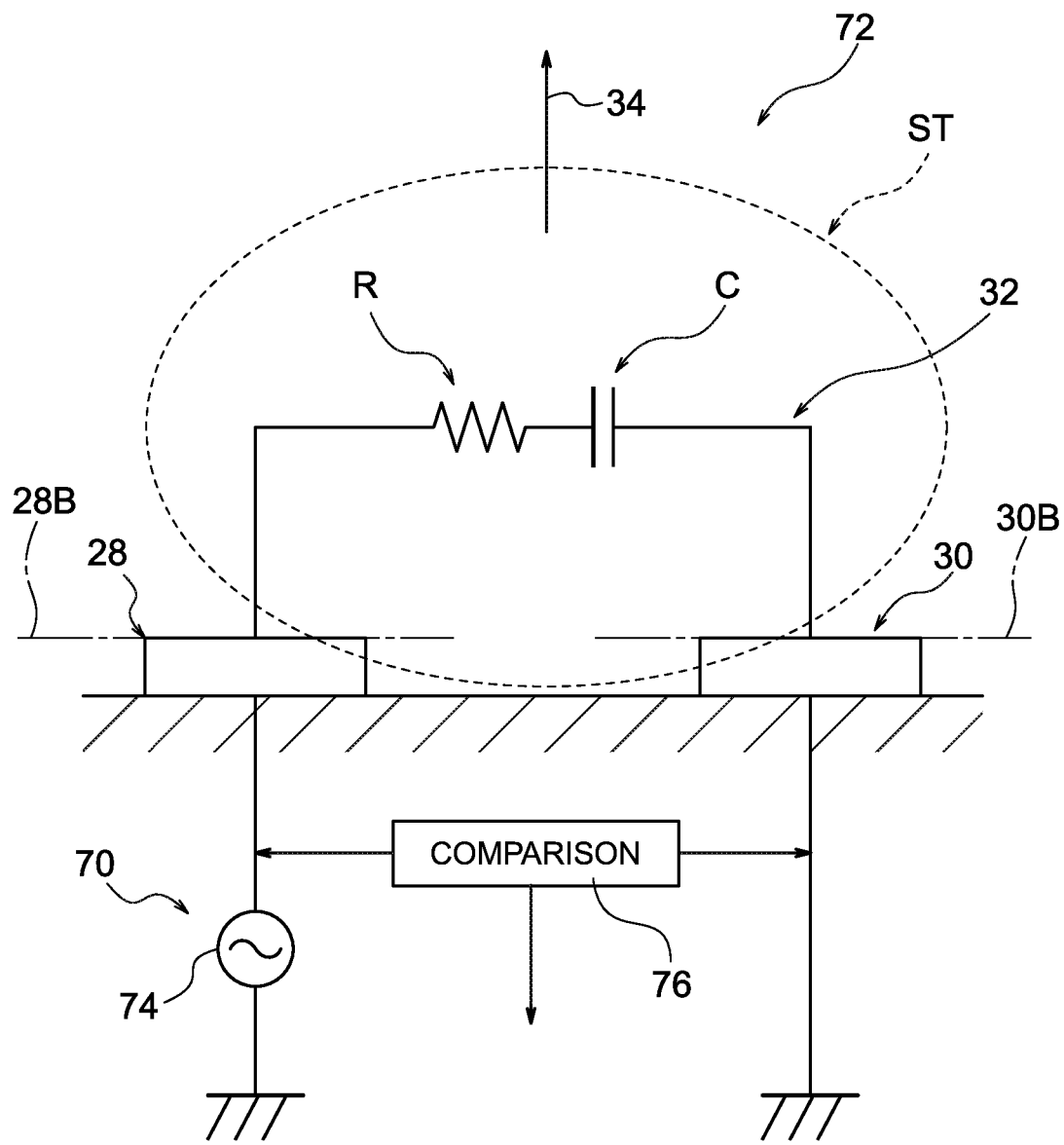
FIG. 7 is an explanatory diagram illustrating an electrical conductivity measurement sensor of the measurement device according to one embodiment.

To describe the electrical conductivity measurement sensor 72 in detail by using an equivalent circuit, the oscillation section 70 of the electrical conductivity measurement sensor 72, as shown in FIG. 7, includes an alternating-current source 74 that outputs an alternating-current signal of a predetermined frequency. The alternating-current source 74 applies an alternating-current signal to the first electrode 28.

The reception section 68 (refer to FIG. 5) includes a comparison circuit 76 that compares the alternating-current signal supplied from the alternating-current source 74 to the first electrode 28 with the input signal that is the alternating-current signal input to the second electrode 30. Specifically, the differences in amplitude and phase between an alternating voltage applied to the first electrode 28 and an alternating voltage input to the second electrode 30 via the measurement object ST are acquired as an electrical conductivity and an impedance between the both electrodes 28, 30 and output to the control section 60. This configures an acquisition unit that applies an alternating-current signal to the first electrode 28 and also measures a phase difference between an alternating-current signal output from the first electrode and an input signal input to the second electrode via the measurement object ST to acquire an electrical conductivity of the measurement object ST.

To explain the operation of the electrical conductivity measurement sensor 72, the measurement device 10 is inserted into the measurement object ST, and the measurement object ST is made to contact the both electrodes 28, 30. Then, an alternating-current signal of a predetermined frequency is applied to the first electrode 28, an input signal input to the second electrode 30 via the measurement object ST is measured, and the electrical conductivity is acquired from the magnitude of the amplitude of an alternating voltage that varies with a resistance component R of the measurement object ST. In addition, the impedance is acquired from the phase difference between the alternating voltage output from the first electrode that varies with an electric capacitance C of the measurement object ST and the alternating voltage input to the second electrode via the measurement object ST.

Since an air content and a moisture content contained in the measurement object ST can be grasped from the acquired electrical conductivity and impedance, the moisture content and ionic concentration of the measurement object ST are acquired by comparing these measurement results with a database preliminarily stored in the control section 60. In addition, nutrient elements contained in the measurement object ST are estimated from the moisture content and ionic concentration acquired by using the database.

Note that, this database stores cancel data to prevent the ISFET 36 disposed near the first electrode 28 and the second electrode 30 from affecting the measurement result by the electrical conductivity measurement sensor 72. The control section 60 corrects the measurement result by the electrical conductivity measurement sensor 72 by using the cancel data.

(Operation and Effect)

Next, operation of the present embodiment will be described.

When a state of the measurement object ST, such as soil for growing a crop or nutrient liquid for hydroponic culture, is measured, as shown in FIG. 8, the tip portion of the measurement device 10 is inserted into the measurement object ST, a pH value is measured with the pH sensor 62, and the moisture content and ionic concentration are measured with the electrical conductivity measurement sensor 72.

At this time, the standard electrode 58 in the reference electrode 38 that forms the pH sensor 62 is provided in the rear inclined surface 42 of the housing 12, and the standard electrode 58 exudes the internal liquid 48 to the measurement object ST and applies the standard potential to the measurement object ST. The hydrogen ions ($H^+$) in the measurement object ST applied with the standard potential gather on the sensitive surface 36A of the ISFET 36 provided on the recessed-portion bottom surface 26A of the front inclined surface 24, and a current flows in the ISFET 36 in response to this. This makes it possible to grasp an amount of hydrogen ions of the measurement object ST by measuring an output voltage of the source S of the ISFET 36 and to acquire the pH value of the measurement object ST.

The first electrode 28 and the second electrode 30 of the electrical conductivity measurement sensor 72 are provided on the recessed-portion bottom surface 26A of the front inclined surface 24 and acquire the moisture content and ionic concentration from the change of the input/output waveform of the alternating-current signal applied to the both electrodes 28, 30 to estimate the nutrient elements contained in the measurement object ST.

Here, the reference electrode 38 of the pH sensor 62 is disposed closer to the rear surface 128 of the first electrode 28 than the first virtual plane 28B that forms the same plane as the front surface of the first electrode 28 and closer to the rear surface 130 of the second electrode 30 than the second virtual plane 30B that forms the same plane as the front surface of the second electrode 30. Thereby, the energization path 32 of the electrical conductivity measurement sensor 72 configured to measure the electrical conductivity at the front side 34 of the both virtual planes 28B, 30B does not cross the standard electrode 58 of the reference electrode 38.

Therefore, the reference electrode 38 can perform multilateral measurement while suppressing influence on the measurement of the electrical conductivity measurement sensor 72.

In addition, the reference electrode 38 of the pH sensor 62 is disposed at the rear side 56 of the first electrode 28 and the second electrode 30. Therefore, the standard electrode 58 of the reference electrode 38 is exposed to the rear side 56 of the first electrode 28 and the second electrode 30.

At this time, in a case in which the reference electrode 38 is disposed on a side of the housing 12 in which the electrodes 28, 30 of the electrical conductivity measurement sensor 72 are arranged, the measurement value of the electrical conductivity will be affected by the internal liquid 48 of the reference electrode 38 dispersed in the measurement object ST via the liquid communication portion 54 of the reference electrode 38.

Hence, in the present embodiment, the reference electrode 38 is disposed on the opposite side of the electrodes 28, 30 of the electrical conductivity measurement sensor 72, and thus it is possible to prevent the internal liquid 48 dispersed from the liquid communication portion 54 of the reference electrode 38 from affecting the measurement of the electrical conductivity measurement sensor 72.

In addition, the standard electrode 58 of the reference electrode 38 has a larger contact area with the measurement object ST in comparison with the ISFET 36. Therefore, compared with a case in which the standard electrode 58 of the reference electrode 38 is disposed on a side of the energization path 32 formed by the first electrode 28 and the second electrode 30, it is possible to prevent the first electrode 28 and the second electrode 30 from affecting the measurement of the electrical conductivity.

Hence, it is possible to measure a state of the measurement object ST accurately and multilaterally.

Here, if the measurement values of the moisture content and ionic concentration in the measurement object ST are measured as values different from actual ones and the measurement object ST is managed based on these values, moisture or nutrient elements may be supplied excessively or insufficiently into the measurement object ST. In this case, there may be a fear of affecting growth of agricultural crops.

Hence, in the measurement device 10 according to the present embodiment, since it is possible to measure a state of the measurement object ST accurately and multilaterally, an environment suitable for growth of agricultural crops can be formed.

At this time, the ISFET 36 forming the pH sensor 62 is, as shown in FIG. 8, disposed at the tip side of the first electrode 28 and the second electrode 30 of the electrical conductivity measurement sensor 72. Thereby, the superposition of a measurement region SR1 by the electrical conductivity measurement sensor 72 and a measurement region SR2 by the pH sensor 62 can be suppressed.

In addition, as shown in FIG. 3, the internal liquid 48 from the standard electrode 58 of the reference electrode 38 is exuded to the opposite side of the energization path 32 formed between the first electrode 28 and the second electrode 30. Hence, it is possible to prevent the internal liquid 48 from affecting the measurement result of the electrical conductivity measurement sensor 72 and to suppress variation of influence degree that may occur particularly in a process of spreading of the internal liquid 48.

These can also contribute to improvement of measurement accuracy.

With respect to the virtual line CS that vertically cuts the housing 12 passing through the tip surface 22, which is one example of a vertex or a top surface of the housing 12, the first electrode 28 and the second electrode 30 are provided on the recessed-portion bottom surface 26A that is the first surface at one I side in the intersecting direction K intersecting with the virtual line CS. In addition, the standard electrode 58 in the reference electrode 38 is provided in the rear inclined surface 42 that is the second surface at another T side in the intersecting direction K.

Thereby, the reference electrode 38 can be disposed at the rear side of the first electrode 28 and the second electrode 30, and thus simplification of the configuration can be achieved.

In the present embodiment, the ISFET 36 of the pH sensor 62 is provided on the recessed-portion bottom surface 26A that is the first surface on which the first electrode 28 and the second electrode 30 of the electrical conductivity measurement sensor 72 are provided.

Hence, the measurement of the pH value by the ISFET 36 can be performed at a position close to the measurement region SR1 by the electrical conductivity measurement sensor 72. This can enhance effect by the management reflecting the measurement result in comparison with a case in which the pH value and the moisture content and ionic concentration of the measurement object ST are measured on the opposite side of the measurement device 10.

The sensitive surface 36A of the ISFET 36 is positioned closer to the recessed-portion bottom surface 26A that is the first surface than the first top surface 28A of the first electrode 28 and the second top surface 30A of the second electrode 30.

Thereby, it is possible to separate the energization path 32 of the alternating-current signal flowing between the first top surface 28A of the first electrode 28 and the second top surface 30A of the second electrode 30 from the sensitive surface 36A of the ISFET 36 to the front side 34. Hence, it is possible to prevent the alternating-current signal flowing between the both electrodes 28, 30 from affecting the ISFET 36 and to contribute to improvement of measurement accuracy by the pH sensor 62.

The electrical conductivity of the measurement object ST is acquired by application of the alternating-current signal to the first electrode 28 and by measurement of the phase difference of the alternating-current signal input to the second electrode 30 via the measurement object ST.

This makes it possible to acquire the moisture content and ionic concentration of the measurement object ST and to estimate the nutrient elements contained in the measurement object ST from the moisture content and ionic concentration.

Note that, in the present embodiment, explanation is given by taking, as an example, a case in which the first electrode 28 and the second electrode 30 are provided on the front inclined surface 24 side of the housing 12 formed into the tapered shape, and the standard electrode 58 of the reference electrode 38 is provided on the rear inclined surface 42 side, but the present embodiment is not limited to this.

For example, in a case in which the tip portion of the housing 12 is formed into a spherical surface shape, the first electrode 28 and the second electrode 30 may be provided on a surface at one I side in the intersecting direction K intersecting with the virtual line CS that vertically cuts the housing 12 and the standard electrode 58 of the reference electrode 38 may be provided on a surface at another T side in the intersecting direction K.

In addition, in a case in which the first electrode 28 and the second electrode 30 are provided on a flat surface formed in the spherical housing 12, the standard electrode 58 of the reference electrode 38 may be provided on a surface different from the flat surface. At this time, the first electrode 28 and the second electrode 30 may be provided at one I side of a virtual plane that vertically cuts the housing 12, and the standard electrode 58 of the reference electrode 38 may be provided at another T side.

What is claimed is:

1. A measurement device comprising:
a first electrode and a second electrode that are configured to form an energization path via a measurement object at a front side and measure an electrical conductivity of the measurement object; and
a reference electrode and an ISFET that are configured to measure a pH value of the measurement object,
wherein a standard electrode of the reference electrode is disposed at a rear side of the first electrode and the second electrode.

2. The measurement device according to claim 1, wherein, with respect to a virtual line that vertically cuts a housing passing through a vertex or a top surface of the housing, the first electrode and the second electrode are provided on a first surface at one side in an intersecting direction intersecting with the virtual line and the standard electrode of the reference electrode is provided on a second surface at another side in the intersecting direction.

3. The measurement device according to claim 2, wherein the ISFET is provided on the first surface.

4. The measurement device according to claim 3, wherein a sensitive surface of the ISFET is positioned closer to the first surface than a top surface of the first electrode and a top surface of the second electrode.

5. The measurement device according to claim 1, further comprising
an acquisition unit that is configured to apply an alternating-current signal to the first electrode and measure a phase difference of an alternating-current signal that is input to the second electrode via the measurement object to acquire an electrical conductivity of the measurement object.

6. A measurement device comprising:
a first electrode that has a front surface contacting a measurement object and outputs an alternating-current signal;
a second electrode that has a front surface contacting the measurement object and receives the alternating-current signal output from the first electrode as an input signal; and
a reference electrode disposed closer to a rear surface of the first electrode than a first virtual plane that forms the same plane as the front surface of the first electrode and closer to a rear surface of the second electrode than a second virtual plane that forms the same plane as the front surface of the second electrode.

7. The measurement device according to claim 6, wherein a standard electrode of the reference electrode is disposed closer to a rear surface of the first electrode than a first virtual plane that forms the same plane as the front surface of the first electrode and closer to a rear surface of the second electrode than a second virtual plane that forms the same plane as the front surface of the second electrode.

* * * * *